US007833257B2

(12) United States Patent
Walsh, Jr. et al.

(10) Patent No.: US 7,833,257 B2
(45) Date of Patent: Nov. 16, 2010

(54) APPARATUS AND METHODS FOR OPTICAL STIMULATION OF THE AUDITORY NERVE

(75) Inventors: Joseph I. Walsh, Jr., Evanston, IL (US); E. Duco Jansen, Nashville, TN (US); Agnella Izzo, Evanston, IL (US); Claus-Peter Richter, Skokie, IL (US)

(73) Assignees: Northwestern University, Evanston, IL (US); Vanderbilt University, Nashville, TN (US)

( * ) Notice: Subject to any disclaimer, the term of this patent is extended or adjusted under 35 U.S.C. 154(b) by 1068 days.

(21) Appl. No.: 11/274,061

(22) Filed: Nov. 14, 2005

(65) Prior Publication Data

US 2006/0161227 A1 Jul. 20, 2006

Related U.S. Application Data

(60) Provisional application No. 60/627,060, filed on Nov. 12, 2004.

(51) Int. Cl.
*A61N 5/06* (2006.01)
(52) U.S. Cl. .......................................... 607/88; 607/89
(58) Field of Classification Search .................... 607/88, 607/89; 128/898
See application file for complete search history.

(56) References Cited

U.S. PATENT DOCUMENTS

| | | | | |
|---|---|---|---|---|
| 3,821,510 A | * | 6/1974 | Muncheryan | 219/121.79 |
| 5,788,711 A | * | 8/1998 | Lehner et al. | 606/130 |
| 6,161,046 A | * | 12/2000 | Maniglia et al. | 607/57 |
| 6,374,143 B1 | * | 4/2002 | Berrang et al. | 607/137 |
| 2002/0002391 A1 | * | 1/2002 | Gerdes | 607/89 |
| 2003/0236458 A1 | * | 12/2003 | Hochman | 600/431 |
| 2004/0148021 A1 | * | 7/2004 | Cartledge et al. | 623/2.37 |
| 2006/0129210 A1 | * | 6/2006 | Cantin et al. | 607/88 |

OTHER PUBLICATIONS

Link, R., et al. Heterodyne-Interferometer for in-situ and in-vivo vibration measurements in the ear, Feb. 1995, Proc. SPIE, vol. 2329, pp. 58-64.*

(Continued)

*Primary Examiner*—Henry M Johnson, III
*Assistant Examiner*—Jeffrey B Lipitz
(74) *Attorney, Agent, or Firm*—Tim Tingkang Xia; Morris, Manning & Martin, LLP

(57) ABSTRACT

A cochlear implant placed in a cochlea of a living subject for stimulating the auditory system of the living subject, where the auditory system comprises auditory neurons. In one embodiment, the cochlear implant includes a plurality of light sources, $\{L_i\}$, placeable distal to the cochlea, each light source, $L_1$, being operable independently and adapted for generating an optical energy, $E_i$, wherein i=1, . . . , N, and N is the number of the light sources, and delivering means placeable in the cochlea and optically coupled to the plurality of light sources, $\{L_i\}$, such that in operation, the optical energies $\{E_i\}$ generated by the plurality of light sources $\{L_i\}$ are delivered to target sites, $\{G_i\}$, of auditory neurons, respectively, wherein the target sites $G_1$ and $G_N$ of auditory neurons are substantially proximate to the apical end and the basal end of the cochlea, respectively.

21 Claims, 10 Drawing Sheets

(a)

(b)      (c)

OTHER PUBLICATIONS

Michalski, W., et al. Preliminary report on influence of argon laser on electrophysiology of cochlea in guinea pigs, Sep. 1996, Proc. SPIE, vol. 3188, pp. 62-66.*

Zharov, V. et al. Autonomous Microdevices for Phototherapy, Sep. 2001, Proc. SPIE, vol. 4560, pp. 171-176.*

Michalski, W., et al. Changes of electric cochlear activity of guinea pigs during argon laser stapedotomy, Nov. 2000, Proc. SPIE, vol. 4238, pp. 83-86.*

Robert, D. and Lewin, A. Scanning laser vibrometry applied to the biomechanical study of a small auditory system, 1998, Proc. SPIE, vol. 3411, pp. 564-571.*

* cited by examiner

APPARATUS AND METHODS FOR OPTICAL STIMULATION OF THE AUDITORY NERVE

CROSS-REFERENCE TO RELATED PATENT APPLICATION

This application claims the benefit, pursuant to 35 U.S.C. §119(e), of U.S. provisional patent application Ser. No. 60/627,060, filed Nov. 12, 2004, entitled "OPTICAL STIMULATION OF THE AUDITORY NERVE," by Joseph T. Walsh, E. Duco Jansen, Agnella Izzo and Claus-Peter Richter, which is incorporated herein by reference in its entirety.

STATEMENT AS TO RIGHTS UNDER FEDERALLY-SPONSORED RESEARCH

This invention was made with Government support under Contract No. FA9550-04-1-0045 awarded by the United States Department of Defense of the United States. The Government has certain rights in this invention.

Some references, which may include patents, patent applications and various publications, are cited in a reference list and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [5] represents the 5th reference cited in the reference list, namely, Geier L V, Norton S. The effect of limiting the number of Nucleus 22 cochlear implant electrodes programmed on speech perception. *Ear Hear* 1992; 13:340-348.

FIELD OF THE INVENTION

The present invention relates generally to the stimulation of neural tissues. More specifically, the present invention relates to apparatus and methods for optical stimulation of the auditory system of a living subject.

BACKGROUND OF THE INVENTION

Neural prosthetic devices are artificial extensions to the body that restore or supplement nervous system function that was lost during disease or injury. Particular success has been realized in the cochlear prostheses development. The devices bypass damaged hair cells in the auditory system by direct electrical stimulation of the auditory nerve. Multiple-electrode cochlear implants are designed to stimulate discrete spiral ganglion cell populations along the cochlea. Stimulating discrete spiral ganglion cell populations in a cochlear implant user's ear is similar to the encoding of small acoustic frequency bands in a normal-hearing person's ear. Thus, it is possible to restore what is commonly thought of as the tonotopic organization of the normal acoustically stimulated cochlea; that is, high frequency tones activate neurons at the base of the cochlea, while low pitch tones stimulate neurons towards the cochlear apex [3-9]. However, the assumption that discrete neural populations can be electrically activated is not always true. It is widely assumed that stimuli applied between closely spaced bipolar electrodes can locally stimulate spiral ganglion cells, whereas widely spaced electrode pairs will lead to broad electric fields and will result in wide areas of neural activation [1, 10]. Nevertheless, for closely spaced electrode pairs at high current levels, a broad region of auditory neurons is activated [10, 11]. Consequently, when two neighboring electrodes are stimulated, a portion of each electric field overlaps, resulting in a population of spiral ganglion cells that are stimulated by both electrodes. If two electrodes stimulate the same neural population, sound sensation encoded via these two electrode contacts might be confused or might even be indistinguishable and this will reduce the number of independent channels of information that can be conveyed to the cochlear implant user. This limitation is based on fundamental physical principles of electrical stimulation that even the best electrode design has not yet overcome.

An important objective in implant electrode design is to maximize the spatial selectivity of stimulation. Several approaches to measure the spatial selectivity of stimulation were reported. In cochlear implant users, impedance measurements on neighboring electrodes were used to estimate the current spread along scala tympani [12-15]. In animal experiments, electrodes were placed at several locations in scala tympani and outside the cochlea. The impedances between each possible pair of electrodes were determined. The current path in the cochlea then was estimated using a lumped element model [3, 16-21]. In another series of experiments, a measuring wire was inserted into the cochlea prior to insertion of the cochlear implant electrode [20, 21]. Stepwise retraction of the measuring electrode allowed the measurement of the potential distribution along the cochlear implant electrode. Again, lumped element models were employed to determine the current path in the cochlea. The common conclusion from all of these experiments was that a large amount of the current injected into the cochlea that was intended for discrete stimulation of the spiral ganglion cells spreads along the scala tympani, thereby non-selectively stimulating broad populations of spiral ganglion cells.

The number of frequency bands required to transmit speech information accurately is an important measurement used in optimization of multiple-electrode stimulation of the cochlea. Shannon et al. [3] and Turner et al. [22] used acoustic models to study the speech information transmitted by fixed filter speech processing schemes. They assessed the optimal number of filter bands to be used as well as the number of cochlear implant electrodes to be stimulated. For quiet listening conditions, a normal-hearing listener could obtain near-normal speech recognition with a four-channel processor. Although these results were confirmed by other groups [23, 24], for noisy listening conditions four channels were not sufficient. It has been estimated that at least twelve independent channels are necessary. Work with cochlear implants demonstrated that speech recognition scores increased with increasing number of electrodes [6, 25-29]. Interestingly, speech recognition scores increased with the number of electrode contacts used, but only up to seven to ten contacts [25]. Normal hearing listeners, in contrast, continued to improve in speech recognition as the number of spectral bands was increased beyond ten. The puzzling aspect of the aforementioned data is that even the best performing cochlear implant users appear to be limited to the equivalent of seven to ten "spectral channels". Although there are other factors, such as the brand of the cochlear implant device and warping in the spectral-tonotopic mapping, the primary factor limiting speech recognition scores seems to be electrode interaction [7]. The use of laser light to stimulate spiral ganglion cells could be one step towards a more discrete stimulation of the auditory system, thus providing an increased number of independent sub-populations of spiral ganglion cells for speech processing.

Therefore, a heretofore unaddressed need exists in the art to address the aforementioned deficiencies and inadequacies.

SUMMARY OF THE INVENTION

In one aspect, the present invention relates to a system for stimulating auditory neurons of a living subject, where the auditory neurons are associated with spiral ganglion cells of the living subject. In one embodiment, the system includes a sound-proofing space for placing auditory neurons of the living subject, a light source for generating an optical energy with a wavelength in a range from 0.5 μm and 10 μm, delivering means optically coupled to the light source for delivering the generated optical energy along an optical path to a target site of auditory neurons to evoke compound action potential (hereinafter "CAP") therein, a monitoring means in communication with the target site of auditory neurons for recording the evoked CAP, and a controller in communication with the light source and the monitoring means for controlling the light source and the monitoring means.

The light source is capable of generating a signal that causes the controller to generate a control signal to trigger the monitoring means to record the evoked CAP. In one embodiment, the light source comprises a tunable laser. In one embodiment, the optical energy generated by the optical source includes a pulsed laser beam with a pulse duration in a range from 1 μs to 10 μs. The laser beam may have a radiant exposure no more than 5.0 J/cm$^2$, more preferably no more than 2.0 J/cm$^2$. In one embodiment, the optical energy is delivered with a repetition rate no more than 2,000 Hz.

In one embodiment, the delivering means includes a number of glass slabs, where each glass slab is movably placed in the optical path of the optical energy for adjusting the intensity of the optical energy to the target site of auditory neurons. When a glass slab is placed in the optical path, it absorbs an amount of the optical energy, and the intensity of the optical energy reachable to the target site of auditory neurons is reduced accordingly, and when a glass slab is moved away from the optical path, the intensity of the optical energy reachable to the target site of auditory neurons is increased accordingly. The delivering means further includes a probe having a working end through which the optical energy is delivered to the target site of auditory neurons, where the working end of the probe is distanced from the target site of auditory neurons. The probe may have at least one optical fiber. The delivering means may also include a movable stage operably coupled to the controller, wherein the probe is mounted to the movable stage so that the probe is movable with the movable stage three-dimensionally to deliver the optical energy selectively to a target site of auditory neurons. In one embodiment, the system may further include a heating element in thermal contact with the at least one optical fiber for warming the at least one optical fiber to a working temperature.

In another embodiment, the delivering means includes a first optical means for directing the optical energy to a desired direction, and a second optical means for focusing the optical energy directed by the first optical means to a target site of auditory neurons, wherein the first optical means and the second optical means are positioned along an optical path of the optical energy. The first optical means comprises an optical reflector, and the second optical means comprises an optical lens.

In another aspect, the present invention relates to a method for stimulating auditory neurons of a living subject. In one embodiment, the method has the steps of generating optical energy with a wavelength in a range from 0.5 μm and 10 μm, delivering the generated optical energy to a target site of auditory neurons, and monitoring CAP evoked within the target site of auditory neurons responsive to the optical energy.

In one embodiment, the optical energy comprises a pulsed laser beam generated by a tunable laser. The optical energy has intensity between a first intensity threshold and a second intensity threshold that is greater than the first intensity threshold. In one embodiment, the first intensity threshold is a stimulation threshold, and the second intensity threshold is an ablation threshold. The ratio of the second intensity threshold to the first intensity threshold is a function of a wavelength of the optical energy.

The present invention, in yet another aspect, relates to a cochlear implant placeable in a cochlea of a living subject for stimulating the auditory system of the living subject, where the auditory system comprises auditory neurons. In one embodiment, the cochlear implant comprises a carrier having a first end, a second end and a body defined therebetween. In one embodiment, the carrier is formed with silicone.

The cochlear implant further comprises a plurality of light sources, $\{L_i\}$. Each of the plurality of light sources $\{L_i\}$ has a radiant cross-section area, $A_i$, is operable independently and is embedded in the body of the carrier for generating an optical energy, $E_i$, where i=1, 2, . . . , N, N is the number of the light sources and $A_1 \leq A_2 \leq \ldots \leq A_N$. The plurality of light sources $\{L_i\}$ are spatially aligned in an array in the body of the carrier such that, as implanted, light sources $L_1$ and $L_N$ are proximate to the apical end and the basal end of the cochlea, respectively. In one embodiment, the plurality of light sources $\{L_i\}$ are connected with wires that are embedded in the body of the carrier. Each of the plurality of light sources $\{L_i\}$ may include a laser, or a light emitting diode. Other light sources may also be utilized to practice the invention.

In one embodiment, the optical energy $E_i$ generated by the light source $L_i$ includes a pulsed laser beam with a pulse duration, $\tau_i$, in a range from 1 μs to 10 ms. In another embodiment, the optical energy $E_i$ generated by the light source $L_i$ includes a light beam with a wavelength, $\lambda_i$, in a range from 0.5 μm to 10 μm. The wavelength of a light beam is preferably chosen such that the absorption depth of the light beam is matched to the anatomic structure of the target auditory neurons. In an alternative embodiment, the optical energy $E_i$ generated by the light source $L_i$ includes a light beam with a radiant exposure, $\sigma_i$, no more than 5.0 J/cm$^2$, more preferably no more than 1.0 J/cm$^2$. The optical energy $E_i$ generated by the light source $L_i$, in one embodiment, is delivered with a repetition rate, $\beta_i$, no more than 2,000 Hz.

Moreover, the cochlear implant comprises delivering means optically coupled to the plurality of light sources, $\{L_i\}$, for individually delivering an optical energy $E_i$ generated by a light source $L_i$ to a corresponding target site of auditory neurons. In one embodiment, the delivering means includes a plurality of optical means, $\{F_i\}$, where each optical means, $F_i$, is optically coupled to a corresponding light source $L_i$ for delivering the optical energy $E_i$ generated by the corresponding light source $L_i$ to a corresponding target site of auditory neurons. In one embodiment, each of the plurality of optical means, $\{F_i\}$, comprises at least one of mirrors and lenses.

Additionally, the cochlear implant may further comprise a processor in communications with the plurality of light sources $\{L_i\}$ for controlling the plurality of light sources $\{L_i\}$ individually or in coordination.

In a further aspect, the present invention relates to a cochlear implant placeable in a cochlea of a living subject for stimulating the auditory system of the living subject, where the auditory system comprises auditory neurons. In one embodiment, the cochlear implant comprises a plurality of light sources, $\{L_i\}$, placed distal to the cochlea when implanted, each light source, $L_i$, being operable independently and adapted for generating an optical energy, $E_i$, wherein i=1, 2, 3, . . . , N, and N is the number of the light sources, and delivering means placed in the cochlea and optically coupled to the plurality of light sources, $\{L_i\}$ such that in operation, the optical energies $\{E_i\}$ generated by the plurality of light sources $\{L_i\}$ are delivered to target sites, $\{G_i\}$, of auditory neurons, respectively, wherein the target sites $G_1$ and $G_N$ of auditory neurons are substantially proximate to the apical end and the basal end of the cochlea, respectively.

In one embodiment, the delivering means comprises a plurality of optical fibers, $\{F_i\}$. Each of the plurality of optical fibers $\{F_i\}$ has a radiant cross-section area, $A_i$, and is coupled to a corresponding light source $L_i$ for delivering the optical energy $E_i$ generated by the corresponding light source $L_i$ to a corresponding target site $G_i$ of auditory neurons, where i=1, 2, . . . , N, and $A_1 \leq A_2 \leq \ldots \leq A_N$. In one embodiment, each of the plurality of optical fibers $\{F_i\}$ has a working end through which the optical energy $E_i$ generated by the corresponding light source $L_i$ is deliverable to the corresponding target site $G_i$ of auditory neurons, where the working end of each of the plurality of optical fiber $F_i$ comprises a beveling tip, a notching tip, or a focusing tip. The delivering means may also comprise at least one of a mirror, lens, prism and any combination of them for focusing the optical energy $E_i$ generated by the corresponding light source $L_i$ onto the corresponding target site $G_i$ of auditory neurons.

Additionally, the cochlear implant may include a processor in communications with the plurality of light sources $\{L_i\}$ for controlling the plurality of light sources $\{L_i\}$ individually or in coordination.

In yet a further aspect, the present invention relates to a method for stimulating the auditory system of the living subject, wherein the auditory system comprises auditory neurons. In one embodiment, the method includes the step of using a cochlear implant placed into the auditory system. The cochlear implant comprises a plurality of light sources, $\{L_i\}$, each light source, $L_i$, being operable independently and adapted for generating an optical energy, $E_i$, wherein i=1, 2, 3, . . . , N, and N is the number of the light sources, and delivering means optically coupled to the plurality of light sources, $\{L_i\}$ for individually delivering an optical energy $E_i$ generated by a light source $L_i$ to a corresponding target site of auditory neurons. The method further includes the step of operating the plurality of light sources $\{L_i\}$ individually or in coordination.

In one embodiment, the delivering means comprises a plurality of optical fibers, each optical fiber having a working end through which the optical energy $E_i$ generated by the light source $L_i$ is deliverable to a corresponding target site of auditory neurons. In another embodiment, the delivering means comprises a plurality of optical means, each optical means having at least one of a mirror, lens, prism, and any combination of them.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, and wherein.

DETAILED DESCRIPTION OF THE INVENTION

Figure 1:
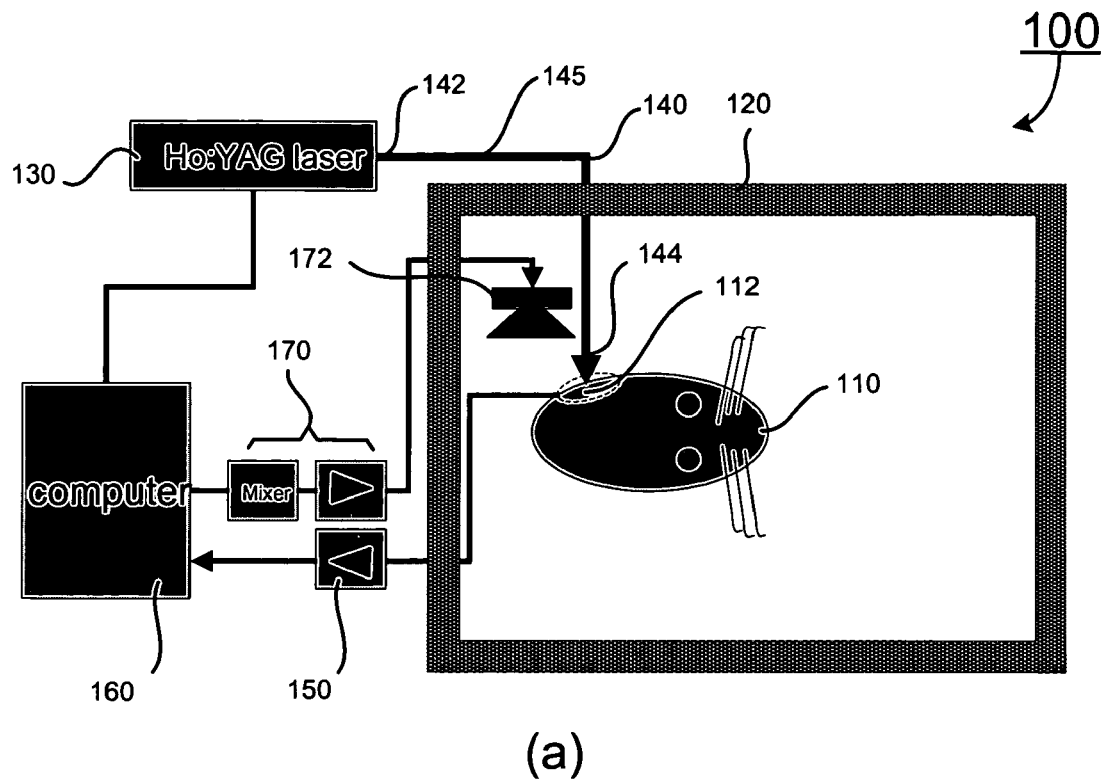
FIG. 1 shows schematically (a) a system for optical stimulating the auditory system of a living subject according to an embodiment of the present invention, (b) a partial portion of delivering means used in the system, and (c) another partial portion of delivering means used in the system.
Figure 1:
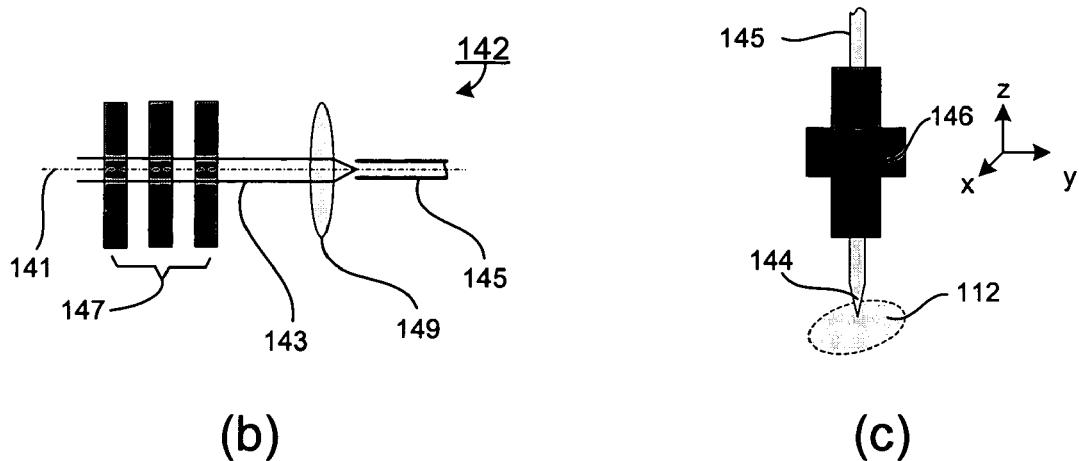

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the term "living subject" refers to a human being such as a patient, or an animal such as a lab testing rat, gerbil, monkey or the like.

As used herein, the term "auditory system" refers to the sensory system for the sense of hearing in a living subject.

As used herein, the term "compound action potential" and its acronym "CAP" refer to the electric response of nerve fibers or muscle tissues to its stimulation such as electrical stimuli, optical stimuli, and/or acoustic stimuli.

As used herein, the term "nerve fiber" refers to a portion of the neuron, namely the axon, which carries action potentials from one end of the neuron to the other. The cochlear nerve fibers originate from neurons of the spiral ganglion and project peripherally to cochlear hair cells and centrally to the cochlear nuclei (cochlear nucleus) of the brain stem. They mediate the sense of hearing.

As used herein, the term "spiral ganglion" refers to the sensory ganglion of the cochlear nerve. The cells of the spiral ganglion send fibers peripherally to the cochlear hair cells and centrally to the cochlear nuclei (cochlear nucleus) of the brain stem.

As used herein, the term "target site" refers to populations or a portion of neurons or nerve cells, including, but not limited to, auditory neurons.

The term "cochlea," as used herein, refers to a spiral-shaped cavity of the inner ear that resembles a snail shell and contains nerve endings essential for hearing.

The cochlea includes three fluid-filled chambers: scala tympani and scala vestibuli (both of which contain perilymph), and scala media (which contains endolymph). The scala tympani and the scala vestibuli are contiguous with each other, merging at the tip of the snail shell, the helicotrema. The stapes transmits vibrations to the fenestra ovalis (oval window) on the outside of the cochlea, which vibrates the perilymph in the scala vestibule. This in turn vibrates the endolymph in the scala media, thus causing movements of the hair bundles of the hair cells, which are acoustic sensor cells that convert vibration into electrical potentials. The hair cells are arranged in four rows in the organ of Corti along the entire length of the cochlear coil. Three rows consist of outer hair cells (OHCs) and one row consists of inner hair cells (IHCs). The IHCs provide the main neural output of the cochlea. The outer hair cells, instead, mainly receive neural input from the brain, which influences their motility as part of the cochlea's mechanical pre-amplifier.

The term "hair cells", as used herein, refers to the sensory cells of the auditory system in all vertebrates. In mammals, the hair cells are located within the cochlea's organ of Corti. They derive their name from the tufts of stereocilia that protrude from the apical surface of the cell, a structure known as the hair bundle. Mammalian hair cells come in two anatomically and functionally distinct types: the outer and inner hair cells. Damage to these hair cells results in decreased hearing sensitivity, i.e. sensorineural hearing loss.

The term "cochlear implant", as used herein, refers to a device that is placed into scala tympani of the cochlea to provide sound per eption for deaf individuals. The cochlea is a snail-like structure buried deeply within the temporal bone, located on either sides of the skull. During cochlear implant surgery, the inner ear is approached from the back to insert the stimulating electrode into scala tympani.

A curvilinear incision is made parallel to and just behind the crease of the ear. The incision is continued until the temporal bone is reached. High-speed otologic drill is employed to remove the bone until the landmarks are available. A small window, facial recess, is opened in the back of the bony ear canal to gain access to the cochlea. A stable landmark on the cochlea, a round window, can be seen from this approach. Using a small drill, an opening to the bony cochlea is made into the round window. The opening is named cochleostomy. Through the cochleostomy, the cochlear duct residing within the bony cochlea is opened to allow insertion of the cochlear implant. After the implant is inserted, the cochleostomy is packed with locally harvested tissue to re-seal it. Incisions are closed in layers to complete the surgery.

OVERVIEW OF THE INVENTION

The present invention, among other things, discloses apparatus and methods for optical stimulating auditory nerve of a living subject and optical cochlear implants placeable in the cochlea of a living subject for optical stimulation of the auditory system of the living subject. The present invention is a novel technological breakthrough in auditory system stimulation that, in one aspect, uses low intensity infrared laser light to elicit CAPs. Optical stimulation of the auditory system can circumvent or overcome many of the limitations of electrical stimulation, including lack of spatial specificity of stimulation and electrical artifacts that limit data analysis and make simultaneous stimulation and recording from adjacent nerve fibers difficult. Optically induced neural CAPs are spatially precise, highly controlled and artifact-free, generated using energies well below tissue ablation threshold.

Referring in general to FIGS. 1(a)-1(c), and particularly to FIG. 1(a) first, a system 100 for stimulating auditory neurons 112 of a living subject 110 includes a sound-proofing booth 120 for placing auditory neurons 112 of the living subject 110, a light source 130 for generating an optical energy, delivering means 140 optically coupled to the light source 130 for delivering the generated optical energy along an optical path 141 to a target site 112 of auditory neurons to evoke a CAP therein, a monitoring means 150 in communication with the target site 112 of auditory neurons for recording the evoked CAP, and a controller 160 in communication with the light source 130 and the monitoring means 150 for controlling the light source 130 and the monitoring means 150. The light source 130 is capable of generating a signal that can cause the controller 160 to generate a control signal to trigger the monitoring means 150 to record the evoked CAP. In one example, the living subject is a gerbil that is placed in the sound-proofing booth 120, and auditory neurons to be stimulated are associated with spiral ganglion cells of the gerbil.

In the exemplary embodiment shown in FIG. 1, the light source 130 includes a Holmium:YAG (hereinafter "Ho: YAG") laser 130. The optical energy generated by the Ho:YAG laser 130 is in the form of a pulsed laser beam 143 with a wavelength about $\lambda = 2.12$ μm, and a pulse duration about $\tau_p = 250$ μs. The delivering means 140 has a probe such as an optical fiber 145 for receiving the optical energy 143 and delivering it towards the target site 112 of auditory neurons. The controller 160 is in the form of a computer.

The Ho:YAG laser 130 is controlled via external power supply. The repetition rate of the Ho:YAG laser 130, which is about 1-10 Hz, and preferably 2 Hz, is controlled via a pulse-forming network that is within the power supply. A remote switch for a shutter within a laser cavity of the Ho:YAG laser 130 can be used for allowing an operator to block all optical output while still exciting the laser cavity. The energy of the laser beam 143 can be modified by placing a number of heat (infrared) absorbing glass slabs 147 in the optical path 141 of the laser beam 143 before being optically coupled into the optical fiber 145, as shown in FIG. 1(b). When a glass slab 147 is placed in the optical path 141, it absorbs an amount of the laser beam 143, and the energy of the laser beam 143 reachable to the target site 112 of auditory neurons is reduced accordingly, and when a glass slab 147 is moved away from the optical path 141, the energy of the laser beam 143 reachable to the target site 112 of auditory neurons is increased accordingly. The energy of the laser beam 143 reachable to the target site 112 of auditory neurons is typically in the range of about 0.005-0.1 $J/cm^2$. The optical fiber 145 is sized in a diameter about $d = 100$ μm, is flat polished, and has a working end 144 through which the laser beam 143 is delivered to the target site 112 of auditory neurons. The working end 144 of the optical fiber 145 is distanced away from the target site 112 of auditory neurons, that is, the optical stimulation of auditory neurons is non-invasive, contact-free stimulation. The optical fiber 145 is passed into the sound-proof booth 120 through an opening formed on the sound-proof booth 120 and is mounted on a movable linear x-y-z translator 146, as shown in FIG. 1(c). The movable linear x-y-z translator 146 can be operably coupled to the computer 160 and is capable of moving in three (x, y, and z) dimensions. Alternatively, the linear x-y-z translator 146 can be moved around manually, through, for example, a matching threaded nut and threaded bolt mechanism. By moving the linear x-y-z translator 146, the optical energy (laser beam) 143 can be delivered to a target site of interest, such as a target site of auditory neurons, through the working end 144 of the optical fiber 145. Typically, the optical fiber 145 is directed through an opening in the bulla and inserted through the round window, and directed towards the modiolus of the cochlea of the gerbil. To prevent hearing loss, a heating wire coil (not shown) can be utilized to wrap around the optical fiber 145 to heat it. In one example, the fiber 145 is heated to about 37° C. Operably, a trigger signal, generated by the Ho:YAG laser 130 at a fixed amount of time before each laser pulse, is sent to the computer 160; the computer 160 then generates a signal to trigger the monitoring means 150 for data acquisition of CAP recording. The CAP recording for the optical stimulation is made with a recording electrode that is hooked onto the bony rim of the round window.

Optical and acoustic stimuli can be delivered simultaneously or independently to the gerbil 110, if necessary. As shown in FIG. 1(a), the acoustic stimuli is implemented with an acoustic source 170 connected to the computer 160 and a speaker 172 connected to the acoustic source 170, and placed in the sound-proofing booth 120 and proximate to but not directly directed at, as the optical stimulus is, the target site 112 of auditory neurons of the gerbil 110.

Other light sources such as a laser for wavelengths in the V, visible and infrared range, an LED light source and an LCD light source may also be employed to practice the current invention. Note that although the embodiment shown in FIG. 1 has a single-fiber arrangement, a multiple-fiber configuration can be used to practice the present invention as well. Additionally, other delivering means including, but not limited to, optical reflectors, optical lenses, prisms can also be utilized to direct a laser/light beam to a target site of auditory neurons of the gerbil for optical stimulation.

One of embodiments of the present invention relates to a method for stimulating auditory neurons of a living subject. The method has the steps of generating an optical energy with a wavelength in a range from 0.5 μm and 10 μm, delivering the generated optical energy to a target site of auditory neurons, and monitoring the CAP evoked within the target site of auditory neurons responsive to the optical energy. The optical energy is in a range between a stimulation threshold and an ablation threshold for the auditory neurons of the living subject. Preferably, the intensity of the optical energy is far below the ablation threshold.

Figure 2:
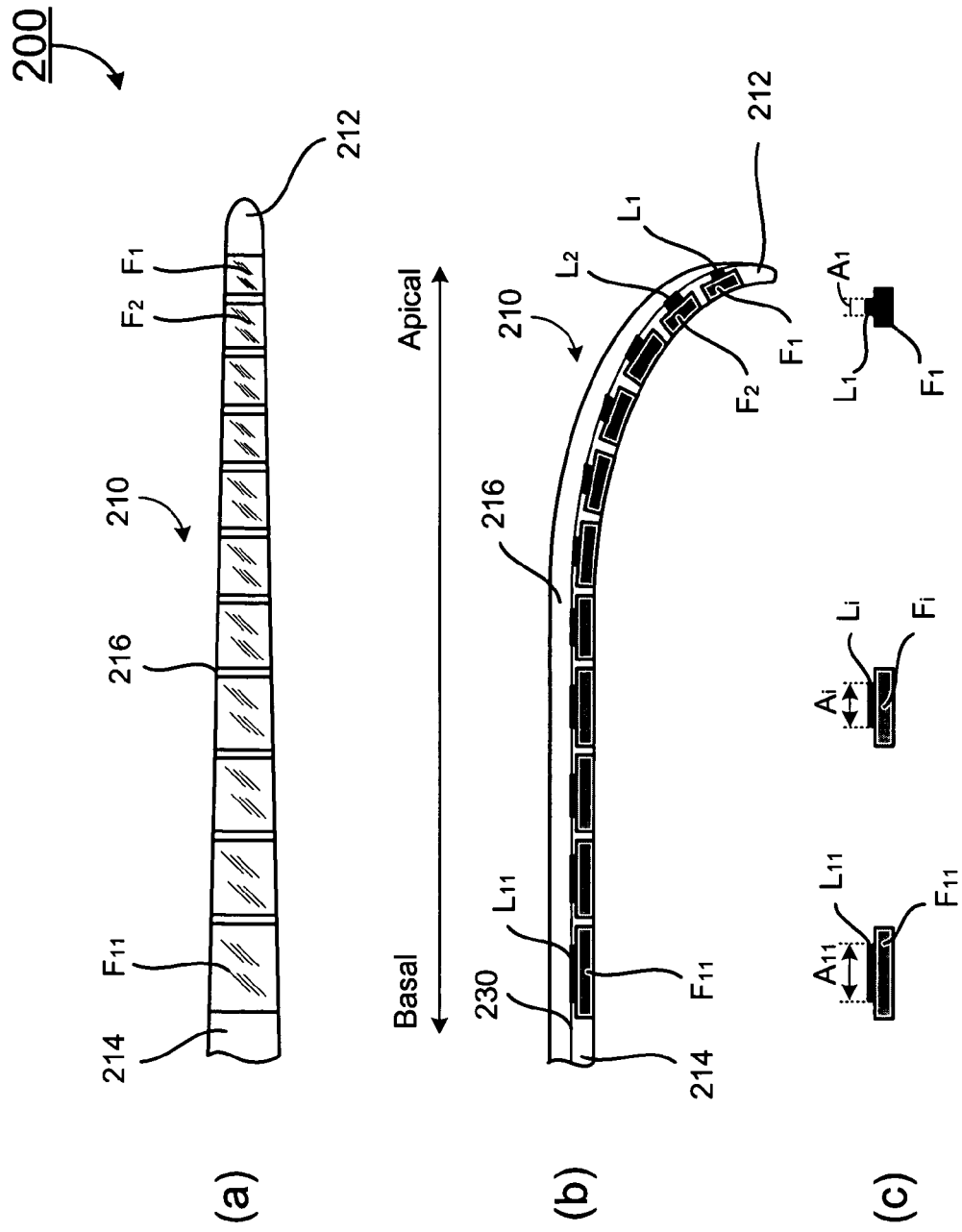
FIG. 2 shows schematically a cochlear implant for optical stimulating auditory system of a living subject according to one embodiment of the present invention: (a) a bottom view, (b) a cross-sectional view, and (c) a partially cross-sectional view.

Referring now to FIG. 2, a cochlear implant 200 includes a carrier 210, a plurality of light sources, $\{L_i\}$, embedded into the carrier 210, and delivering means optically coupled to the plurality of light sources, $\{L_i\}$, for individually delivering an optical energy $E_i$ generated by a light source $L_i$ to a corresponding target site of auditory neurons, where $i = 1, 2, \ldots, N$, and N is the number of the light sources. The cochlear implant 200 can be operably implanted in a cochlea of a living subject for stimulating the auditory system such as auditory neurons of the living subject. The carrier 210 has a first end 212, a second end 214 and a body 216 defined therebetween and is formed with silicone or the like. Each of the plurality of light sources $\{L_i\}$ has a radiant cross-section area, $A_i$, is operable independently and is embedded in the body 216 of the carrier 210 for generating an optical energy, $E_i$, where $A_1 \leqq A_2 \leqq \ldots \leqq A_N$. The plurality of light sources $\{L_i\}$ are spatially aligned in an array in the body 216 of the carrier 210 such that, as implanted, light sources $L_1$ and $L_N$ are proximate to the apical end and the basal end of the cochlea, respectively, as shown in FIGS. 2(a)-2(c). Consequently, the cochlear implant 200 in the basal end portion of the cochlea have a larger radiating cross-section area than those at the apical end portion of the cochlea so as to better match the size of the tissue within which the neuron population is contained at those cochlear locations. Each light source $L_i$ is contacted by an individual wire and can be addressed independently. The wires 230 are running as a bundle across the backside of the cochlear implant 200. The wires 230 are embedded in the silicone carrier 210 that provides the electrodes shape and insulates individual elements from each other and from the surrounding medium. The light sources $\{L_i\}$ can include any number of individual light sources, and each can be a laser, an LED light source, or an LCD light source. For example, eleven light sources $L_1, L_2, \ldots$ and $L_{11}$ are employed and are aligned into a cochlear implant array in the exemplary embodiment shown in FIG. 2. The eleven light sources $L_1$, $L_2, \ldots$ and $L_{11}$ are operable individually, or in coordination, by a processor (not shown).

The optical energy $E_i$ generated by the light source $L_i$ includes a pulsed laser beam. Operating parameters, such as wavelength, pulse duration and pulse repetition rate, of the pulsed laser beam may vary with individuals and species. In one embodiment, the pulsed laser beam has a wavelength, $\lambda_i$, in a range from 0.5 μm to 10 μm, more preferably about 2.12 μm, and a pulse duration, $\tau_i$, in a range from 1 μs to 10 ms, more preferably about 250 μs. The repetition rate, $\beta_i$, of the pulsed laser beam is no more than 2,000 Hz. The radiant exposure, $\sigma_i$, of the pulsed laser beam to a corresponding target site of auditory neurons is no more than 5.0 J/cm$^2$, more preferably no more than 1.0 J/cm$^2$.

The delivering means includes a plurality of optical means, $\{F_i\}$, and each optical means $F_i$ is optically coupled to a corresponding light source, $\{L_i\}$, for individually delivering optical energy $E_i$ generated by the light source $L_i$ to a corresponding target site of auditory neurons. Each of the plurality of optical means $\{F_i\}$ has at least one of mirrors and lenses. As shown in FIG. 2, the delivering means has eleven optical means $F_1, F_1, \ldots$ and $F_{11}$, and each is mounted and fixed within the silicone carrier 210. Alternatively, each optical means may contain optic fiber to deliver optical energy.

Figure 3:
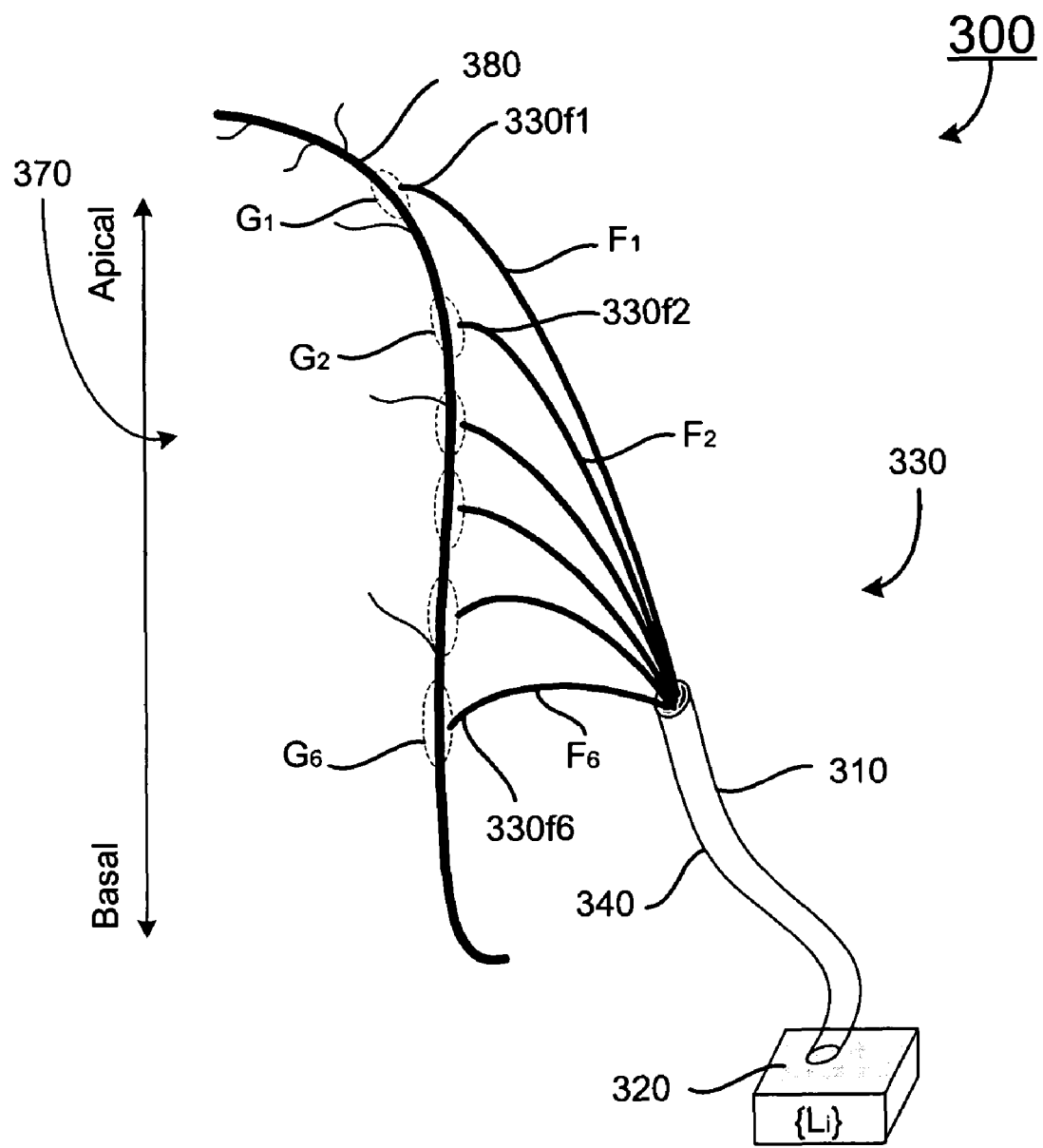
FIG. 3 shows schematically a cochlear implant for optical stimulating the auditory system of a living subject according to another embodiment of the present invention.

FIG. 3 shows another embodiment of a cochlear implant 300 of the present invention. The cochlear implant 300 can be operably placed in a cochlea 370 of a living subject for stimulating the auditory system such as auditory neurons 380 of the living subject. In this embodiment, the cochlear implant 300 has a plurality of light sources $\{L_i\}$ 320 placeable distal to the cochlea 370 in operation, for instance, under the scalp or within a behind-the-ear housing for a speech processor. Alternatively, the plurality of light sources can be in a box positioned, for example, on the hip. Each light source, $L_i$, is operable independently and adapted for generating optical energy, $E_i$, wherein i=1, 2, 3, ..., N, and N is the number of the light sources. A transcutaneous or percutaneous connection for the optical cochlear implant setup may be utilized.

The cochlear implant 300 also includes delivering means 330 that is placeable in the cochlea 370 and optically coupled to the plurality of light sources $\{L_i\}$ 320 such that in operation, the optical energies $\{E_i\}$ generated by the plurality of light sources $\{L_i\}$ 320 are delivered to target sites, $\{G_i\}$, of auditory neurons, respectively, where the target sites $G_1$ and $G_N$ of auditory neurons are substantially proximate to the apical end and the basal end of the cochlea, respectively. The delivering means 330 comprises a plurality of optical fibers, $\{F_i\}$. Alternatively, hollow waveguides can also be utilized to practice the present invention. Each of the plurality of optical fibers $\{F_i\}$ has a radiant cross-section area, $A_i$, and is optically coupled to a corresponding light source $L_i$ for delivering the optical energy $E_i$ generated by the corresponding light source $L_i$ to a corresponding target site $G_i$ of auditory neurons, where $A_1 \leq A_2 \leq \ldots \leq A_N$. Thus, the radiating cross-section area of the optical fibers would decrease from the basal end portion to the apical end portion of the cochlea 370. Each of the plurality of optical fibers $\{F_i\}$ has a working end through which the optical energy $E_i$ generated by the corresponding light source $L_i$ is deliverable to the corresponding target site $G_i$ of auditory neurons. The working end of each of the plurality of optical fiber $\{F_i\}$ may have a beveling tip, a notching tip, or a focusing tip.

As shown in FIG. 3, the plurality of optical fibers $\{F_i\}$ has six individual fibers $F_1, F_2, \ldots F_6$ that are pre-curved for better insertion into the cochlea 370. These fibers $F_1, F_2, \ldots$ and $F_6$ are housed in a silicone carrier 310 to form an optical cable 340 that is optically coupled to the light source $\{L_i\}$ 320. At the working end (330/1, 330/2, ..., or 330/6) of a fiber (F1, F2, ... or F6), an optical energy such as laser pulses is deflected towards a corresponding target structure ($G_1$, $G_2, \ldots$, or $G_6$) for stimulation of the target structure. To achieve this, mirrors or prisms may be employed.

In one aspect, the present invention also provides a method for stimulating the auditory system of the living subject. The method includes the steps of using a cochlear implant, as disclosed above, placeable into the auditory system, and operating the plurality of light sources $\{L_i\}$ of the cochlear implant individually or in coordination to generate one or more light beams to stimulate the auditory system.

While a pulsed laser system has been used in the embodiments set forth above, other types of lasers can also be utilized to practice the present invention.

Methods, Examples and Implementations of the Invention

Without intent to limit the scope of the invention, exemplary methods and their related results according to the embodiments of the present invention are given below. Note again that titles or subtitles may be used in the examples for convenience of a reader, which in no way should limit the scope of the invention. Moreover, certain theories are proposed and disclosed herein; however, in no way they, whether they are right or wrong, should limit the scope of the invention.

The following exemplary experiments were conducted at the Northwestern University and the Vanderbilt University. All data reported herein were based on measurements in gerbils and rats although successful measurements were performed in frogs as well. The procedures for care and use of the animals were in accordance with animal protocols approved by the Institutional Animal Care and Use Committee (IACUC) of the Northwestern University and the Vanderbilt University, respectively.

Laser stimulation: Optical stimulation was performed using laser pulses generated from a Ho:YAG laser (Laser 1-2-3, Schwartz Electro-Optics, Inc., Concord, Mass.), which emits 2.12-μm radiation, with a pulse duration of 250 μs. The Ho:YAG laser can be operated between 1-10 Hz repetition rates. For optical stimulation experiments shown below, the Ho:YAG laser was conducted at a repetition rate of about 2 Hz. The laser pulses generated by the Ho:YAG laser were coupled via lens into a low-OH, silica bare fiber (FIP series, Polymicro Technologies, LLC, Phoenix, Ariz.), with a core diameter of about 100 μm. The spatial beam profile out of the fiber had been quantified as near-Gaussian. Before the experiments, the optical energy output of the fiber was measured with an energy sensor (J25-110, Molectron Detector Inc., Portland, Oreg.). The pulse energy of the Ho:YAG laser was controlled by varying the number of heat absorbing glass slabs placed in the beam path, rather than changing the driving voltage on the laser control panel, thus the spatial beam profile was constant. The temperature of the laser rod was controlled at 14±1° C. by a recirculating water chiller (CFT-33, Neslab Instruments, Inc., Portsmouth N.H.).

The response of the auditory nerve to the optical energy stimulation was sensed using stainless steel needle electrodes placed at the rim of the round window for recording auditory nerve CAPs of a gerbil. The reference electrode was placed in a pocket under the skin of the opposite jaw. Acoustically evoked CAPs served to monitor cochlea functions throughout the experiments. Furthermore, optically-evoked CAPs were used to quantify responses of the auditory system to the laser stimulation.

Other light sources such as another YAG laser, a semiconductor diode laser or laser for wavelengths in the UV, visible and infrared, a tunable free electron laser (FEL), an LED light source and an LCD light source may also be employed to practice the current invention. Additionally, if it is desired to use a wavelength around 4-7 micrometers, then a lead-salt laser, or an optical parametric oscillator (or amplifier or generator) may be used.

Detailed animal surgical procedure: The gerbils were anesthetized by an initial intraperitoneal injection of sodium pentobarbital (80 mg/kg body weight). Maintenance doses were 17 mg/kg bodyweight and were given throughout an experiment whenever the animal showed signs of increasing arousal, which were assessed every 30 minutes by a paw withdrawal reflex. After the animal was fully anesthetized, breathing was facilitated by performing a tracheotomy and securing a length of PE90 tubing into the opening in the trachea. The animal then was positioned, belly up, on a heating pad used to maintain body temperature at 38° C., and its head was stabilized in a heated head holder. A dermal incision was made from the lower right jaw to the right shoulder in order to expose the right submandibular gland, which was subsequently ligated and removed. The muscles attached to the bulla and to the styloid bone were carefully dissected. Next, the bulla was opened to allow access to the cochlea. A silver electrode was hooked onto the bony rim of the round window of the cochlea, and a ground electrode was placed under the skin at the left jaw. After cutting the cartilaginous outer ear canal, a speculum (for the sound delivery system) was cemented with dental acrylic to the bony part of the outer ear canal. The surgical platform containing the animal was then moved onto a vibration isolation table in a soundproof booth. Two chest electrodes were attached to monitor heart rate, and a high-frequency tweeter (Beyer 770 Pro) was coupled to the speculum at the ear canal. A series of auditory nerve CAP threshold curves was obtained across frequency in order to determine baseline cochlear function. The end of the optical fiber was placed as close as possible to the modiolus.

Monitoring of cochlear functions: CAP thresholds were defined as sound levels required for a 20 μV N1/P1 amplitude (A1) at a given stimulus frequency and was determined using a modified tracking procedure. Acoustical stimuli used to determine the CAP thresholds comprised tone bursts of 12 ms in duration, including the 1 ms rise and 1 ms fall time. The CAP threshold determination was made by comparing the voltage (A2) measured from the round window membrane electrode in a time window of 6 ms duration that began with the onset of the tone burst and contained the CAP. To reduce the contribution of cochlear microphonics, responses to 32 consecutive tone-burst presentations delivered in opposite phase were averaged. Moreover, the overall noise of the recordings was reduced by bandpass filtering the response with a set of custom programmable filters, the highpass set to 600 Hz and the lowpass set to 3000 Hz. At each stimulus frequency, the initial sound level was approximately 95 dB SPL (sound pressure level). Sound level then was decreased five times according to the following equation: 20 log(A2/A1). Threshold was assigned when the given criterion (20±2 μV) was reached. It took about 15 minutes to determine CAP thresholds for a frequency range of five octaves with a resolution of 6 steps per octave. The highest frequency was 50 kHz.

Optical Stimulation of the Auditory Nerve

Figure 4:
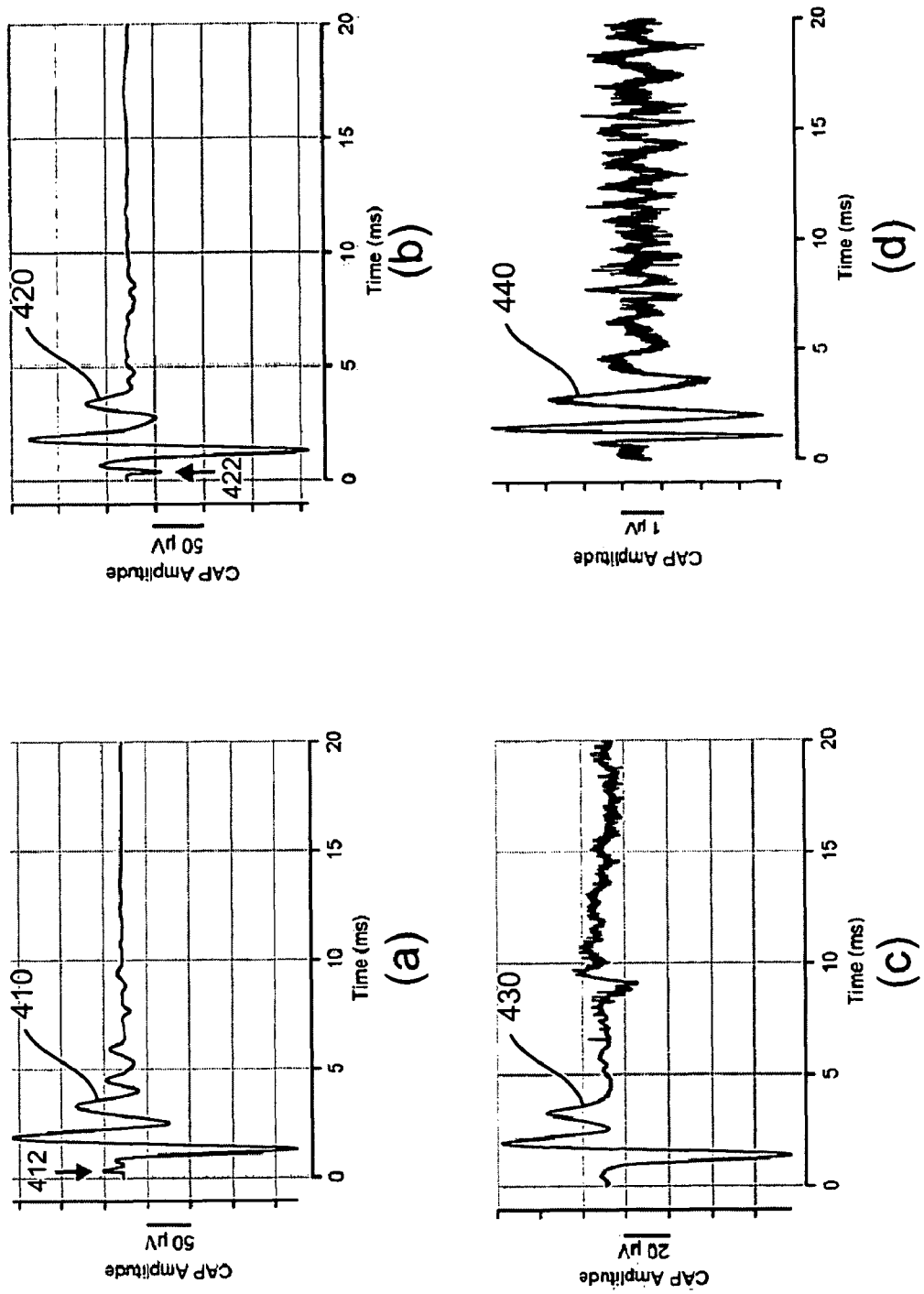
FIG. 4 shows compound action potentials (CAPs): (a) evoked with an acoustic click stimulus, (b) evoked with an acoustic click stimulus that is 180° out of phase with the acoustic click stimulus used in (a), (c) evoked with an optical stimulus having the intensity of 0.06 J/cm², and (d) evoked with an optical stimulus having the intensity of 1.6 J/cm² in a long-term deafened animal according to one embodiment of the present invention.

In rat sciatic nerve studies, stimulation threshold values of 0.04 J/cm$^2$ were found. Both acute and survival studies of extended stimulation of the sciatic nerve (at least one hour) resulted in no discernable damage on histological analysis. In survival studies, rats retained normal function with no neurological deficit after stimulation. Based on these studies, a set of parameters was formulated to perform feasibility studies of optical stimulation of the auditory nerve in a gerbil. In one embodiment, the optical stimulation of the auditory nerve of the gerbil was conducted with a pulsed Ho:YAG laser with a wavelength $\lambda=2.12$ μm and a pulse duration $\tau_p=250$ μs. The laser beam was delivered to a target site of the auditory nerve of a gerbil with an optical fiber through its working end. Referring to FIG. 4, curve 410 represented the CAP evoked with an acoustic click stimulus, while curve 420 was the CAP evoked with an acoustic click stimulus that was 180° out of phase with the acoustic click stimulus used for obtaining curve 410. Cochlear microphonics (hereinafter "CMs") were indicated by arrows 412 and 422 in FIGS. 4(a) and 4(b), respectively, which indicated that CMs inverted when clicks were presented in opposite phase. Curve 430 showed representative optical stimulation CAP evoked with a light bean having an optical radiant exposure of 0.06 J/cm$^2$. Curve 430 was acquired from the same animal used in curves 410 and 420. Curve 440 showed the CAP evoked with a light bean having an optical radiant exposure of 1.6 J/cm$^2$ in a long-term deafened animal, where complete deafening of the animal was confirmed electro-physiologically and histologically. No CM was shown in the optically evoked CAPs in curves 430 and 440, as shown FIGS. 4(c) and 4(d), respectively. Curves 410 and 420 were averages of 100 stimulus presentations while curves 430 and 440 were averages of ten stimulus presentations.

The exemplary experiments clearly showed that the auditory nerve could be stimulated with a pulsed laser beam. From the perspective of laser-tissue interactions, the Ho:YAG laser output ($\lambda=2.12$ μm, $\tau_p\sim250$ μs) is a compromise between the necessary absorption and penetration of the radiation and yields heating over a time period appropriate for the size of the target (the nerve). Nonetheless, for cochlear implants the wavelengths and pulse duration may need to be optimized.

Parameters of the Laser for Safe Auditory Nerve Stimulation

It is expected that initial values for radiation wavelength, energy, spot size, and repetition rate of a laser beam and placement of an optical fiber to be used for the optical stimulation of the auditory nerve may be further optimized. The evaluation of effects of the parameters of a laser beam generated from a Ho:YAG laser on optical stimulation of the auditory system of gerbils were given below. Surgical access to gerbil cochleae was gained and an optical fiber was placed on the modiolus for the optical stimulation. An optical fiber having a proximal end coupled to the Ho:YAG laser for receiving the laser beam generated by the Ho:YAG laser and a distal, working end directed to the modiolus for delivering the laser beam to target nerves of the auditory system of the gerbil.

Figure 5:
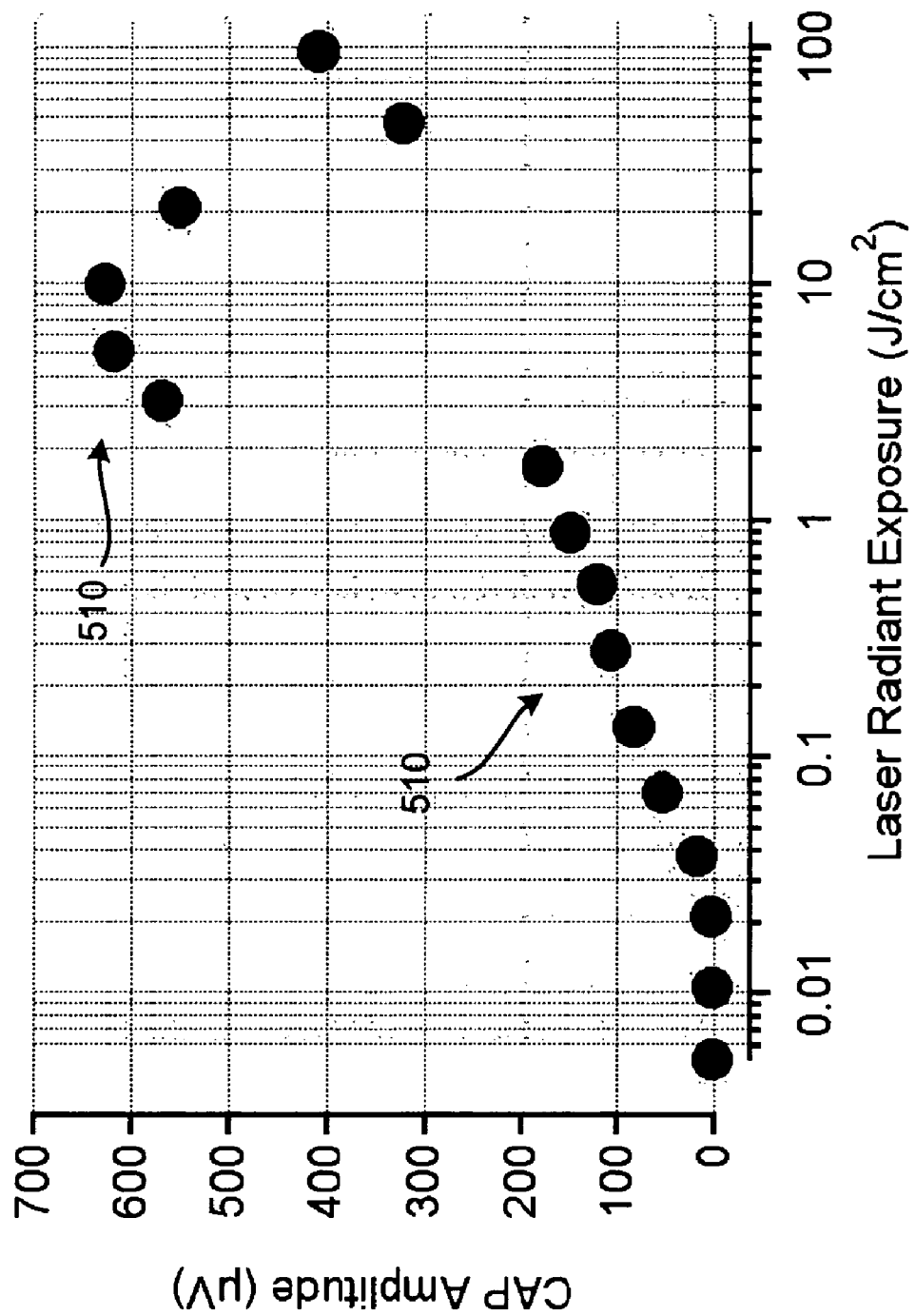
FIG. 5 shows the effect of the laser radiant exposure on the laser induced CAP amplitude according to one embodiment of the present invention.

Varying Energy of Laser (N=4): To determine the range of the laser energy that allows optical stimulation of the auditory nerve without tissue ablation, the output energy of the laser was varied by adding heat absorbing glass slabs immediately before the proximal end of the optical fiber. Each glass slab absorbed roughly 50% of the laser beam's power. In the experiments, the laser energy was increased until cochlear damage was observed, where the cochlear damage was indicated by a decrease of the CAP amplitude. Referring to FIG. 5, effects of the laser energy (radiant exposure, or fluence) on the CAP amplitude 510 were shown. The laser radiant exposure was increased from about 0.01 J/cm$^2$ to 90 J/cm$^2$ in the exemplary experiment, as shown in FIG. 5. The CAP amplitude 510 increased with increasing the laser radiant exposure from about 0.01 J/cm$^2$ to 9 J/cm$^2$. Specifically, as the radiant exposure increased from 0.04 J/cm$^2$ to 2.0 J/cm$^2$, there was a relatively continuous increase in the CAP amplitude 510, while a drastic increase in the CAP amplitude 510 was indicated as the radiant exposure increased from about 2 J/cm$^2$ to 3.1 J/cm$^2$. The CAP amplitudes 510 decreased as the laser radiant exposure is greater than 9 J/cm$^2$. A safe range of at least 30 dB was observed between stimulation threshold and nerve damage. A post-experiment check of the animal revealed that cerebrospinal fluid (CSF) was leaking from the gerbil cochlea, indicating that the laser had made a hole through the modiolar wall.

Note that the laser energy receivable by the target auditory nerve can be varied by other means and/or methods. For example, if a semiconductor laser or an LED is utilized to practice the invention, the optical energy can be changed by changing the driving current of the semiconductor laser or LED.

Varying Distance from the round window (N=4): To estimate effects of orientations and distances of the working end of an optical fiber from the target site of the auditory nerve or spiral ganglion cells on the laser-induced (optically evoked) CAP amplitude therein, the optical fiber was placed through the round window onto the modiolus and had a distance defined between the working end of the optical fiber and target spiral ganglion cells. CAP measurements were taken in 50 μm increments as the fiber was being distanced apart from the modiolus. Two different orientations of the fiber were used at which the fiber was placed: directed perpendicular to the spiral ganglion cells and directed at a shallow angle towards the spiral ganglion cells.

Figure 6:
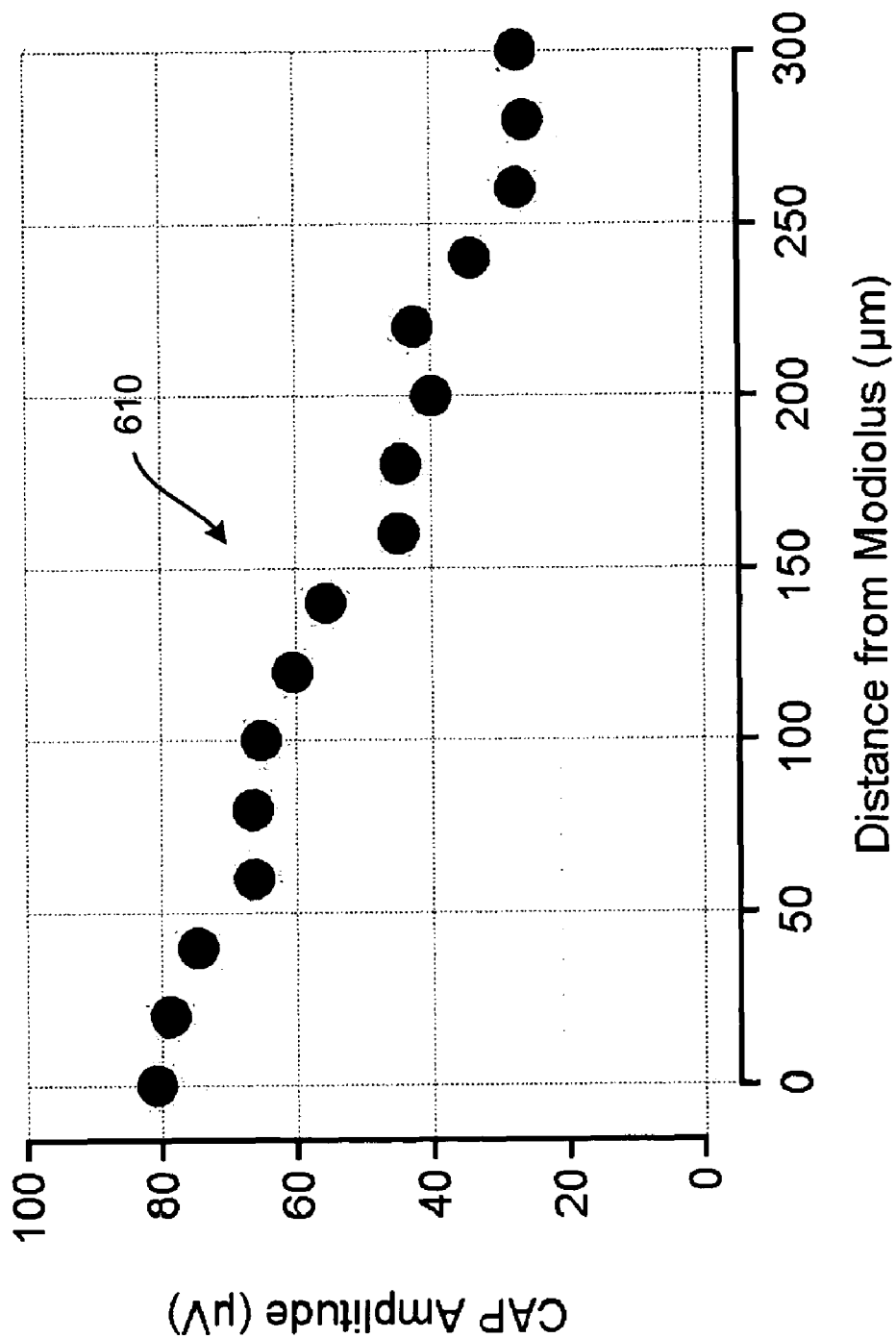
FIG. 6 shows the effect of the fiber distance from the modiolus on the laser-induced CAP amplitude according to one embodiment of the present invention.

When the optical fiber was directed toward the spiral ganglion cells and being distanced apart from the modiolus, the CAP amplitude decreased quickly with increasing the distance. FIG. 6 shows effects of the distance between the working end of the fiber and the modiolus on the laser-induced CAP amplitude 610, where the optical fiber was placed at a shallow angle to the modiolus and the laser operated at radiant exposure of 0.13 J/cm$^2$. Measurements were made at the "zero" position, when the optical fiber was touching bone and at 50 μm increments as the fiber was being distanced apart from the cochlea with a linear translator. The data indicated a steadily decrease in the laser-induced CAP amplitude as the distance increases for the optical fiber being at a shallow angle with respect to the modiolus.

Figure 7:
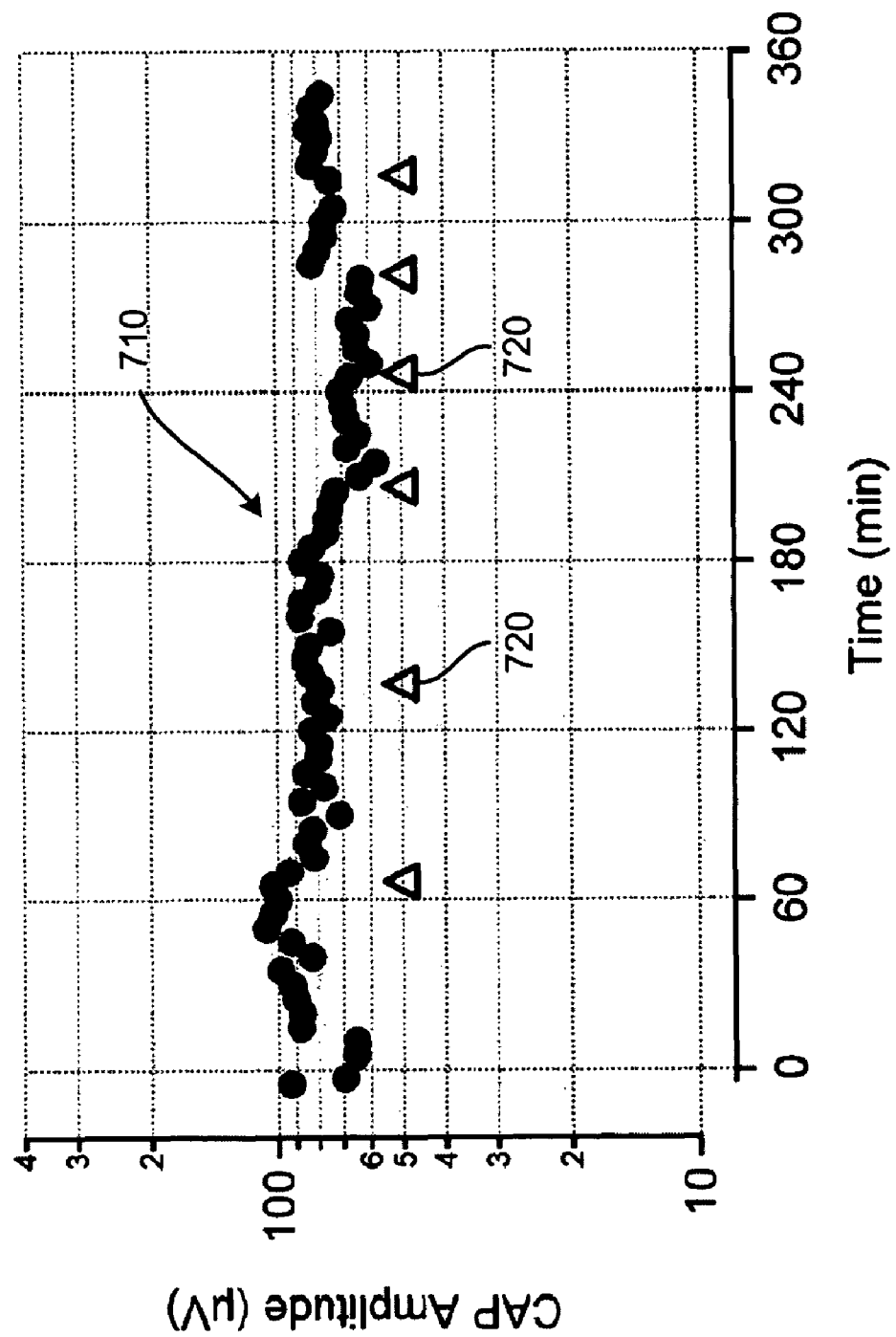
FIG. 7 shows long-term continual optical stimulation of the auditory nerve in a normal hearing animal according to one embodiment of the present invention.

Extended Stimulation Time (N=4): Laser pulses with a pulse duration of 250 μs and a pulse repetition rate of 2 Hz were delivered to the gerbil cochlea continually for a period of 6 hours to evaluate long-term effects of the optical stimulation on auditory functions of the gerbil. Measurements were acquired every 6 minutes. It was unlikely that negative thermal effects from the laser stimulation occurred because the CAP amplitude remained stable during the entire stimulation time. FIG. 7 showed optically evoked CAP 710 for the long-term continual optical stimulation of the auditory nerve in a normal hearing animal. The optical stimulation was lasting over a period of 6 hours and the corresponding optically evoked CAP amplitude 710 was a relatively constant over the period of stimulation, as shown in FIG. 7. The laser was stopped only to administer anesthesia at times 720, which were indicated by the triangles in FIG. 7. In this experiment, the radiant exposure of the laser radiation onto the gerbil cochlea was about 0.06 J/cm$^2$.

CAP responses after acute and long term deafening of the gerbils (N=4): Experiments were designed to test whether pressure waves, possibly induced by the laser, might stimulate the cochlea of the gerbil. For this purpose, a gerbil was acutely deafened using a protocol reported in Ref. [30]. An initial intraperitoneal injection of kanamycin (300 mg/kg) was followed 45 minutes later by an intravenous injection of ethacrynic acid (25 mg/kg). Acoustically and optically evoked CAPs were recorded before and after both drug injections and after euthanizing the animal. The acoustic responses were monitored to document the progress of the gerbil's deafening. The acoustically evoked CAP amplitudes decreased and the corresponding CAP thresholds increased drastically (about 60 dB) within a few minutes after the ethacrynic acid injection. In contrast to the acoustically evoked responses, no significant decreases in the optically evoked CAP amplitudes were observed after the kanamycin or ethacrynic acid injection. As a control, measurements were made after euthanizing the gerbil. No noticeable CAP was present for either acoustic or optical stimulation. In another experiments, a gerbil was chronically deafened by a single Neomycin injection at the amount of about 150 μl, with a neomycin concentration of 180 mg/ml, into the middle ear. Four weeks after the injection, no acoustically evoked CAP could be recorded but the optically evoked CAP were measured. Histological analysis of the cochlea in the long-term deafened animal revealed a complete loss of inner and outer hair cells and severe spiral ganglion cells degeneration. These results indicated that optical stimulation does not involve the hair cells, directly or indirectly, and suggests that the stimulation occurs directly at the auditory neurons.

Figure 8:
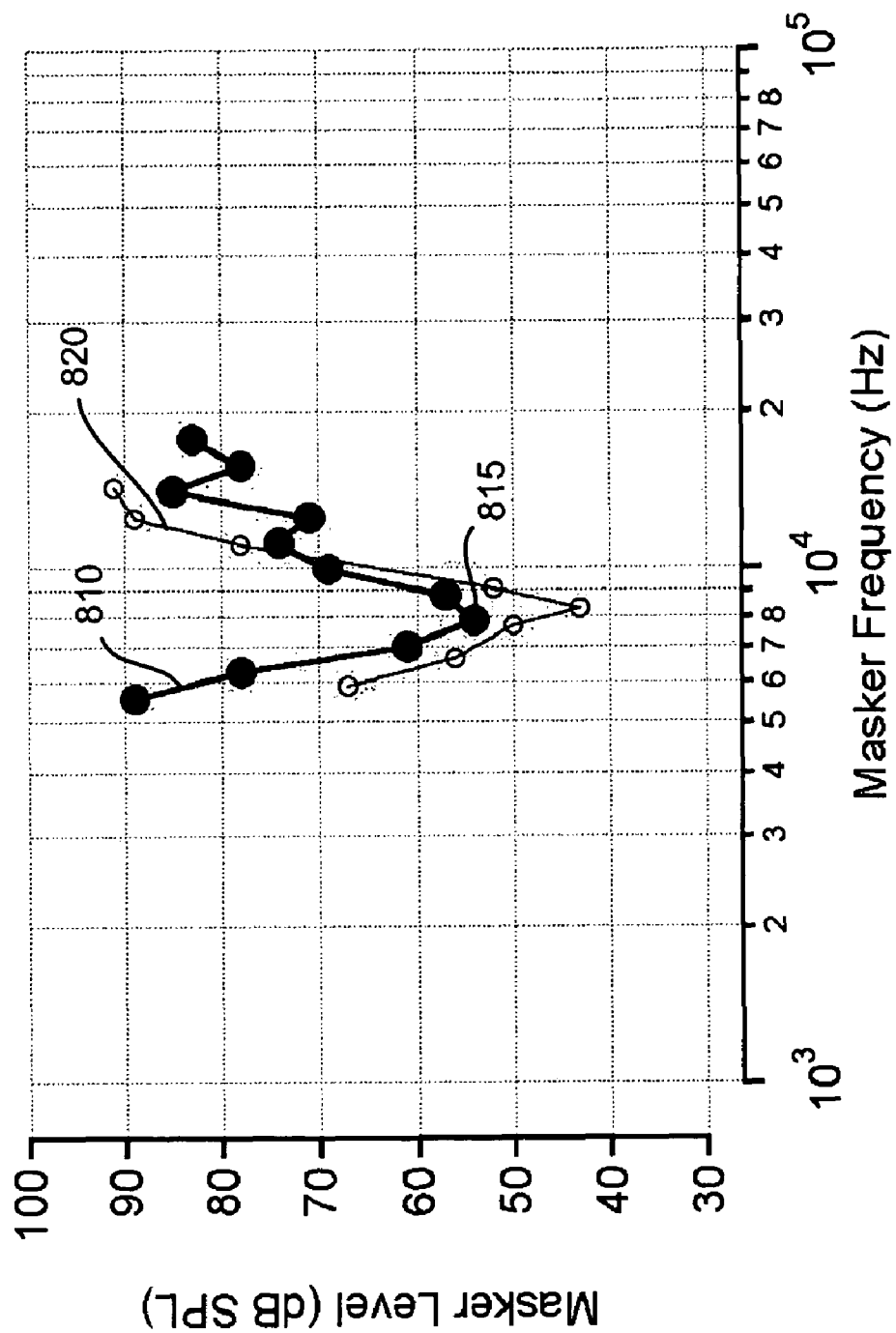
FIG. 8 shows tone-on-light masking curves of optical stimulation of the auditory nerve of a gerbil according to one embodiment of the present invention.

Spatial selectivity determined with tone-on-light masking (N=4): Spatial selectivity for optical stimulation was measured with a masking method, known to those skilled in the art. The optically evoked auditory nerve CAP was masked with a tonal masker. The placement of the optical fiber along the cochlea determined the corresponding best frequency (hereinafter "BF"), and the light energy corresponded to the probe level. An acoustic signal, variable in frequency and level, served as the customary masker. Masker level at a given frequency was changed until the optically evoked CAP was reduced by 3 dB. The resulting tuning curves were similar to tone-on-tone masking curves, indicating a spatially localized optical stimulation of the cochlea. The example indicating a BF of 8 kHz and a $Q_{10dB}$ value of 3.3 was shown in FIG. 8, where optical radiation served as the probe stimulus and acoustic masker sound levels needed to reduce the optically evoked CAP by 3 dB in the tone-on-light masking curve 810. A tuned response with a minimum 815 at 8 kHz was observed. The sharpness of the tuning, calculated as the ratio of the BF of the tuning curve to the bandwidth of the curve 10 dB above the minimum, is 3.3. For reference, a gerbil tone-on-tone tuning curve with a similar BF is shown by curve 820.

Visualization of Spiral Ganglion Cells Activated (N=4)

Figure 9:
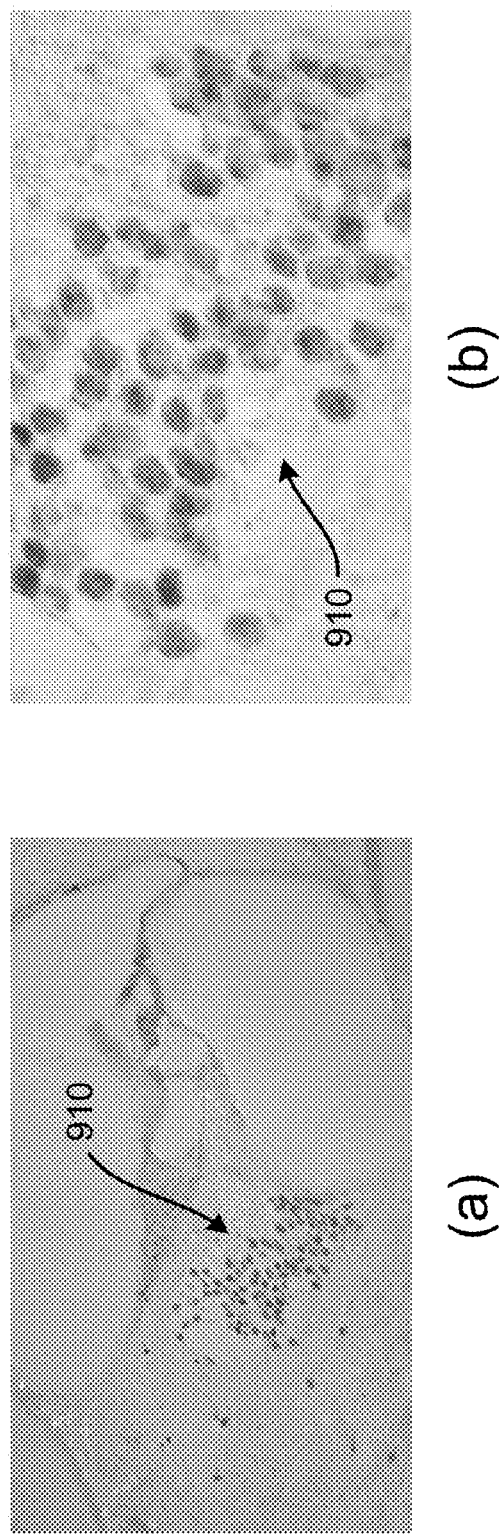
FIG. 9 shows (a) a cross section view of a cochlear turn (about 7 mm from the basal cochlear end) with acoustic stimulation with a 5 kHz tone and subsequent c-fos staining, and (b) a magnified view of the cochlear turn according to one embodiment of the present invention.

The exemplary experiments were performed to demonstrate the ability to measure acoustically, optically and electrically induced c-fos expression, a transiently expressed transcription factor, in the gerbil brainstem and the cochlea. The procedure was the same as one reported in Refs. [31-38]. A representative example of c-fos staining in the cochlea was shown in FIG. 9. Specifically, FIG. 9(a) showed a cross section of a cochlear turn, located about 7 mm from the basal cochlear end, following acoustic stimulation with a 5 kHz tone and subsequent c-fos staining. Nuclei of the spiral ganglion cells were shown as dark circles 910 in FIG. 9(*a*). A magnified view of the spiral ganglion cell nuclei 910 was shown in FIG. 9(*b*).

Figure 10:
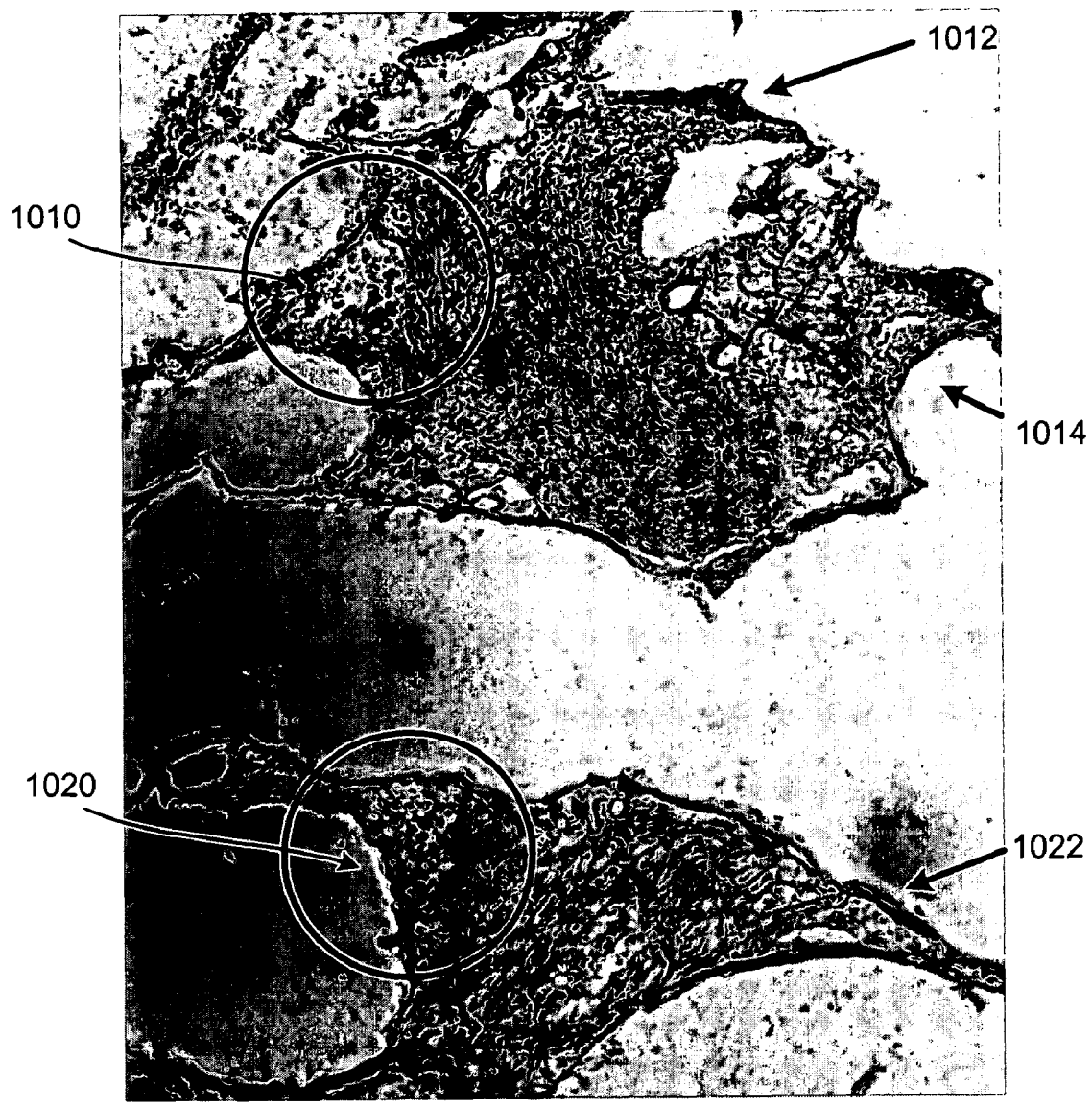
FIG. 10 shows images of spiral ganglion cells of a gerbil with optical stimulation according to one embodiment of the present invention.

For the electric stimulation, a silver electrode sized about 125 µm in diameter was placed through the round window on the modiolus and a return electrode in a pocket under the skin. For the optical stimulation, the optical fiber was placed through the round window to shine the light towards the modiolus. The acoustic stimulation was achieved using a modified BeyerDT770Pro speaker. After the electrodes, or the optical fiber, or the speaker, were placed, the gerbils were kept in quiet for one hour. This time period allowed the c-fos expression to be reduced to a minimum. Next, auditory nerve responses were evoked by either current, light, or sound. Stimulation occurred for 90 minutes to maximally express c-fos. After euthanizing the animals, the brain and the cochleae were harvested for immunohistochemistry. Control animals, which were not stimulated, did not reveal any c-fos staining. The optical stimulation of the cochlea was extremely spatially selective. As shown in FIG. 10, the spiral ganglion cells were stained in the basal turn 1010, directly opposite to the optical fiber's working end and at the middle turn 1020, and the spiral ganglion cells on the contralateral side of the cochlea, indicated by arrows 1012, 1014 and 1022, were not stained. No staining indicated that the cells were not stimulated, while staining for c-fos is a marker for the stimulated spiral ganglion cells. In the exemplary experiment, the laser radiant exposure onto spiral ganglion cells was about 0.015 J/cm$^2$.

The present invention, among other things, discloses a novel approach to efficient, artifact-free stimulation of the auditory neurons using low-level pulsed infrared laser at radiant exposures well below tissue damage threshold and a cochlear implant of using the same. The potential advantage of using light would be a significantly improved spatial resolution of stimulation in the cochlea. Light can be focused toward target structures and is not spread along scala tympani or across turns of the cochlea; such spread occurs with electrical stimulation and is a limitation of contemporary cochlear implants.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1]. Busby P A, Whitford L A, Blarney P J, Richardson L M, Clark G M. Pitch perception for different modes of stimulation using the cochlear multiple-electrode prosthesis. *J Acoust Soc Am* 1994; 95:2658-2669.

[2]. Shannon R V, Fu Q J, Galvin J, 3rd. The number of spectral channels required for speech recognition depends on the difficulty of the listening situation. *Acta Otolaryngol Suppl* 2004:50-54.

[3]. von Békésy G. *Experiments in Hearing*. New York: McGraw-Hill Book Company, 1960.

[4]. Greenwood D D. A cochlear frequency-position function for several species—29 years later. *J Acoust Soc Am* 1990; 87:2592-2605.

[5]. Geier L V, Norton S. The effect of limiting the number of Nucleus 22 cochlear implant electrodes programmed on speech perception. *Ear Hear* 1992; 13:340-348.

[6]. Fishman K E, Shannon R V, Slattery W H. Speech recognition as a function of the number of electrodes used in the SPEAK cochlear implant speech processor. *J Speech Lang Hear Res* 1997; 40:1201-1215.

[7]. Friesen L M, Shannon R V, Baskent D, Wang X. Speech recognition in noise as a function of the number of spectral channels: comparison of acoustic hearing and cochlear implants. *J Acoust Soc Am* 2001; 110:1150-1163.

[8]. Lawson D. New processing strategies for multichannel cochelar prosthesis. *Prog Brain Res* 1993; 97:331-321.

[9]. Lawson D. Speech processors of auditory prostheses. *Third quaterly progress report, NIH Contract Nol-DC-5-2103* 1996.

[10]. van den Honert C, Stypulkowski P H. Single fiber mapping of spatial excitation patterns in the electrically stimulated auditory nerve. *Hear Res* 1987; 29:195-206.

[11]. Frijns J H, de Snoo S L, ten Kate J H. Spatial selectivity in a rotationally symmetric model of the electrically stimulated cochlea. *Hear Res* 1996 May; 95:33-48.

[12]. Black R C, Clark G M, Patrick J F. Current distribution measurements within the human cochlea. *IEEE Trans Biomed Eng* 1981; 28:721-725.

[13]. Black R C, Clark G M, Tong Y C, Patrick J F. Current distribution in cochlear stimulation. *Ann N Y Acad Sci* 1983; 405:137-145.

[14]. Faltys M, Griffith G, Segel P et al. Electric field imaging methodology. *Conference on Implantable Auditory Prostheses*, Pacific Grove Calif., 2001.

[15]. Vanpoucke F, Zarowski A, Casselman J, Frijns J, Peeters S. The facial nerve canal: an important cochlear conduction path revealed by Clarion electrical field imaging. *Otol Neurotol* 2004; 25:282-289.

[16]. von Békésy G. The course pattern of the electrical resistance in the cochlea of the guinea pig (electroanatomy of the cochlea). *JASA* 1951; 23:18-28.

[17]. Suesserman M F. Noninvasive microelectrode measurement technique for performing quantitative, in vivo measurements of inner ear tissue impedances.: University of Washington, 1992.

[18]. Suesserman M F, Spelman F A. Quantitative in vivo measurements of inner ear tissue resistivities: I. In vitro characterization. *IEEE Trans Biomed Eng* 1993; 40:1032-1047.

[19]. Suesserman M F, Spelman F A. Lumped-parameter model for in vivo cochlear stimulation. *IEEE Trans Biomed Eng* 1993; 40:237-245.

[20]. Kral A, Hartmann R, Mortazavi D, Klinke R. Spatial resolution of cochlear implants: the electrical field and excitation of auditory afferents. *Hear Res* 1998; 121:11-28.

[21]. Mortazavi M. Untersuchungen zur Einschrankung des elektrischen Feldes und Verbesserung der Kanaltrennung bei intracochleaerer elektrischer Reizung. Frankfurt am Main: JWG-Universitat, 1995.

[22]. Turner C W, Souza P E, Forget L N. Use of temporal envelop cues in speech recognition by normal and hearing-impaired listeners. *JASA* 1995; 97:2568-2576.

[23]. Hochmair-Desoyer I J, Hochmair E S, Burian K, Stiglbrunner H K. Percepts from the Vienna cochlear prosthesis. *Ann N Y Acad Sci* 1983; 405:292-306.

[24]. Hochmair E S, Hochmair-Desoyer I J. Percepts elicited by different speech-coding strategies. *Ann N Y Acad Sci* 1983; 405:268-279.

[25]. Holmes A, Kemker F J, Merwin G. The effects of varying the number of cohlear implant electrodes on speech perception. *Am J Otol* 1987; 8:240-246.

[26]. Kilney P, Zimmerman-Phillips S, Zwolan T, Kemink J. Effects of channel number and place of stimulation on performance with the cochlear corporation multichannel implant. *Am J Otol* 1992; 13:117-123.

[27]. Blamey P J, Pyman B C, Gordon M et al. Factors predicting postoperative sentence scores in postlinguistically deaf adult cochlear implant patients. *Ann Otol Rhinol Laryngol* 1992; 101:342-348.

[28]. Eddington D K, Rabinowitz W R, Tierney J, Noel V, Whearty M. Speech processors for auditory prostheses. 8*th Quaterly progress report, NIH COntract N*01-*DC*-6-2100 1997.

[29]. McKay C M, McDermott H J, Clark G M. The beneficial use of channel interactions for improvement of speech perception for multichannel cochlear implants. *Australian Journal of Audiology* 1994; 15:20-21.

[30]. Pfennigdorff T. Elektrisch evozierte Potentiale vom Hörnerv: Die Entwicklung einer präopertiven Methode für Cohlea-Implantationen. Frankfurt am Main: Johann Wolfgang Goethe-Universität, 1993.

[31]. Nagase S, Miller J M, Dupont J, Lim H H, Sato K, Altschuler R A. Changes in cochlear electrical stimulation induced c-fos expression in the rat inferior colliculus following deafness. *Hearing Research* 2000; 147:242-250.

[32]. Ehret G, Fisher R. Neural activity and tonotopy in the auditory system visualized by c-fos gene expression. *Brain Research* 1991; 567:350-354.

[33]. Friauf E. Tonotopic order in the adult and developing auditory system of the rat as shown by c-fos immunocytochemistry. *European journal of Neuroscience* 1992; 4:798-812.

[34]. Gleich O, Strutz J. Age-dependent effects of the onset of a conductive hearing loss on the volume of the cochlear nucleus subdivisions and the expression of c-fos in the mongolian gerbil (*Meriones unguiculatus*). *Audiol Neurootol* 1997; 2:113-127.

[35]. Fichtel I, Ehret G. Perception and recognition discriminated in the mouse auditory cortex by c-fos labeling. *Neuroreport* 1999; 10:2341-2345.

[36]. Saito H, Miller J M, Pfingst B E, Altschuler R A. Fos-like immunoreactivity in the auditory brain stem evoked by bipolar intracochlear electrical stimulation: Effects of current level and pulse duration. *Neuroscience* 1999; 91:139-161.

[37]. Wan H, Warburton E C, Kusmierek P, Aggleton J P, Kowalska D M, Brown M W. Fos imaging reveals differential neuronal activation of areas of rat temporal cortex by novel and familiar sounds. *Eur J Neurosci* 2001; 14:118-124.

[38]. Hsu W, Campos-Torres A, Portier F et al. Cochlear electrical stimulation: influence of age of implantation on fos immunocytochemical reactions in the inferior colliculi and dorsal cochelar nuclei of the rat. *J Comp. Neurol* 2001; 438.

What is claimed is:

1. A cochlear implant placeable in a cochlea of a living subject for stimulating the auditory system of the living subject, wherein the auditory system comprises auditory neurons, comprising:
   (a) a carrier having a first end, a second end and a body defined therebetween;
   (b) a plurality of light sources, $\{L_i\}$, each light source, $L_i$, having a radiant cross-section area, $A_i$, and being operable independently and embedded in the body of the carrier for generating an optical energy, $E_i$, wherein $i=1, \ldots, N$, and N is the number of the light sources and $A_1 \leq A_2 \leq \ldots \leq A_N$;
   (c) a processor in communications with the plurality of light sources $\{L_i\}$ for controlling the plurality of light sources $\{L_i\}$ individually or in coordination; and
   (d) delivering means coupled to the plurality of light sources, $\{L_i\}$, for individually delivering an optical energy $E_i$ generated by a light source $L_i$ to a corresponding target site of auditory neurons,
   wherein the plurality of light sources $\{L_i\}$ are spatially aligned in an array in the body of the carrier such that, when implanted, the body of the carrier is positioned between the apical end and the basal end of the cochlea such that the light sources $L_1$ and $L_N$ are proximate to the apical end and the basal end of the cochlea, respectively, hereby radiant exposure area of the target site of auditory neurons in the apical end portion of the cochlea corresponding to the light source $L_1$ is less than that in the basal end portion of the cochlea corresponding to the light source $L_N$.

2. The cochlear implant of claim 1, wherein the plurality of light sources $\{L_i\}$ are connected with wires that are embedded in the body of the carrier.

3. The cochlear implant of claim 1, wherein the delivering means comprises a plurality of optical means, $\{F_i\}$, each optical means, $F_i$, optically coupled to a corresponding light source $L_i$ for delivering the optical energy $E_i$ generated by the corresponding light source $L_i$ to a corresponding target site of auditory neurons.

4. The cochlear implant of claim 3, wherein each of the plurality of optical means, $\{F_i\}$, comprises at least one of mirrors and lenses.

5. The cochlear implant of claim 1, wherein the optical energy $E_i$ generated by the light source $L_i$ comprises a pulsed laser beam with a pulse duration, $\tau_i$, in a range from 1 μs to 10 ms.

6. The cochlear implant of claim 1, wherein the optical energy $E_i$ generated by the light source $L_i$ comprises a light beam with a wavelength, $\lambda_i$, in a range from 0.5 μm to 10 μm.

7. The cochlear implant of claim 1, wherein the optical energy $E_i$ generated by the light source $L_i$ comprises a light beam with a radiant exposure, $\sigma_i$, no more than 5.0 J/cm², more preferably no more than 1.0 J/cm².

8. The cochlear implant of claim 1, wherein the optical energy $E_i$ generated by the light source $L_i$ is delivered with a repetition rate, $\beta_i$, no more than 2,000 Hz.

9. The cochlear implant of claim 1, wherein each of the plurality of light sources $\{L_i\}$ comprises a laser, or a light emitting diode.

10. The cochlear implant of claim 1, wherein the carrier is formed with silicone.

11. A cochlear implant placeable in a cochlea of a living subject for stimulating the auditory system of the living subject, wherein the auditory system comprises auditory neurons, comprising:

(a) a plurality of light sources, $\{L_i\}$, placed distal to the cochlea when implanted, each light source, $L_i$, having a radiant cross-section area, $A_i$, and being operable independently and adapted for generating an optical energy, wherein i=1, ..., N, and N is the number of the light sources and $A_1 \leq A_2 \leq \ldots \leq A_N$;

(b) a processor in communications with the plurality of light sources $\{L_i\}$ for controlling the plurality of light sources $\{L_i\}$ individually or in coordination; and (c) delivering means coupled to the plurality of light sources, $\{L_i\}$ such that in operation, the optical energies $\{E_i\}$ generated by the plurality of light sources $\{L_i\}$ are delivered to target sites, $\{G_i\}$, of auditory neurons, respectively, wherein the target sites $G_1$ and $G_N$ of auditory neurons are substantially proximate to the apical end and the basal end of the cochlea, respectively, hereby radiant exposure area of the target site $G_1$ of auditory neurons in the apical end portion of the cochlea corresponding to the light source $L_1$ is less than that of the target site $G_N$ of auditory neurons in the basal end portion of the cochlea corresponding to the light source $L_N$.

12. The cochlear implant of claim 11, wherein the delivering means comprises a plurality of optical fibers, $\{F_i\}$, each optical fiber $F_i$ optically coupled to a corresponding light source $L_i$ for delivering the optical energy $E_i$ generated by the corresponding light source $L_i$ to a corresponding target site $G_i$ of auditory neurons.

13. The cochlear implant of claim 12, wherein each of the plurality of optical fibers $\{F_i\}$ has a working end through which the optical energy $E_i$ generated by the corresponding light source $L_i$ is deliverable to the corresponding target site $G_i$ of auditory neurons.

14. The cochlear implant of claim 13, wherein the working end of each of the plurality of optical fiber $F_i$ comprises a beveling tip, a notching tip, or a focusing tip.

15. The cochlear implant of claim 12, wherein the delivering means comprises at least one of a mirror, lens, prism and any combination of them for focusing the optical energy $E_i$ generated by the corresponding light source $L_i$ onto the corresponding target site $G_i$ of auditory neurons.

16. The cochlear implant of claim 11, wherein the optical energy $E_i$ generated by the light source $L_i$ comprises a pulsed laser beam with a pulse duration, $\tau_i$, in a range from 1 μs to 10 ms.

17. The cochlear implant of claim 11, wherein the optical energy $E_i$ generated by the light source $L_i$ comprises a light beam with a wavelength, $\lambda_i$, in a range from 0.5 μm to 10 μm.

18. The cochlear implant of claim 11, wherein the optical energy $E_i$ generated by the light source $L_i$ comprises a light beam with a radiant exposure, $\sigma_i$, no more than 5.0 J/cm$^2$, more preferably no more than 1.0 J/cm$^2$.

19. The cochlear implant of claim 11, wherein the optical energy $E_i$ generated by the light source $L_i$ is delivered with a repetition rate, $\beta_i$, no more than 2,000 Hz.

20. The cochlear implant of claim 11, wherein each of the plurality of light sources $\{L_i\}$ comprises a laser, or a light emitting diode.

21. A method for stimulating the auditory system of the living subject, wherein the auditory system comprises auditory neurons, comprising the steps of:

(a) providing a plurality of light sources, $\{L_i\}$, each light source, $L_i$, having a radiant cross-section area, $A_i$, and being operable independently and adapted for generating an optical energy, $E_i$, wherein i=1, ..., N, and N is the number of the light sources and $A_1 \leq A_2 \leq \ldots \leq A_N$;

(b) operating the plurality of light sources $\{L_i\}$ individually or in coordination to generate a plurality of optical energies, $\{E_i\}$, therefrom, each optical energy $E_i$ generated by a corresponding light source $L_i$; and (c) individually delivering each optical energy $E_i$ to a corresponding target site of auditory neurons, such that radiant exposure area of the target site $G_1$ of auditory neurons is less than that of the target site $G_N$ of auditory neurons.

* * * * *

UNITED STATES PATENT AND TRADEMARK OFFICE
CERTIFICATE OF CORRECTION

PATENT NO. : 7,833,257 B2
APPLICATION NO. : 11/274061
DATED : November 16, 2010
INVENTOR(S) : Joseph T. Walsh, Jr. et al.

It is certified that error appears in the above-identified patent and that said Letters Patent is hereby corrected as shown below:

<u>On the Title Page of the Letters Patent Item 75</u>:

Please delete the name of the first named inventor "~~Joseph I. Walsh, Jr.~~".

Please add the name of the first named inventor -- <u>Joseph T. Walsh, Jr.</u> --.

<u>In the Specification</u>:

In Column 1, Lines 17 to 20 delete:

"~~This invention was made with Government support under Contract No. FA9550-04-1-0045 awarded by United States Department of Defense of the United States. The Government has certain rights in this invention.~~"

Please add:

-- <u>This invention was made with government support under Grant No. FA9550-04-1-0045 awarded by the Department of Defense. The government has certain rights in the invention.</u> --

Signed and Sealed this
Twelfth Day of July, 2011

David J. Kappos
*Director of the United States Patent and Trademark Office*